United States Patent
Nakamura et al.

[11] Patent Number: 5,968,581
[45] Date of Patent: Oct. 19, 1999

[54] DIPEPTIDE DERIVATIVES AND SWEETENING AGENTS

[75] Inventors: Ryoichiro Nakamura; Yusuke Amino; Tadashi Takemoto, all of Kawasaki, Japan

[73] Assignee: Ajinomoto Co., Inc., Tokyo, Japan

[21] Appl. No.: 09/037,870

[22] Filed: Mar. 10, 1998

[30] Foreign Application Priority Data

Mar. 18, 1997 [JP] Japan ..................... 9-064135

[51] Int. Cl.$^6$ .................. A23L 1/236; C07C 229/00
[52] U.S. Cl. .................. 426/548; 562/433; 562/442; 562/450
[58] Field of Search .............. 426/548; 562/433, 562/442, 450, 409

[56] References Cited

U.S. PATENT DOCUMENTS

| | | | |
|---|---|---|---|
| 5,723,165 | 3/1998 | Takemoto et al. | 426/548 |
| 5,723,651 | 3/1998 | Hijiya et al. | 560/169 |
| 5,795,612 | 8/1998 | Takemoto et al. | 426/548 |
| 5,856,579 | 1/1999 | Takemoto et al. | 564/425 |

*Primary Examiner*—Keith D. Hendricks
*Attorney, Agent, or Firm*—Oblon, Spivak, McClelland, Maier & Neustadt, P.C.

[57] ABSTRACT

Novel dipeptide derivatives, such as N-3,3-dimethylbutyl-α-L-aspartyl-α-methyl-L-phenylalanine methyl ester and N-3,3-dimethylbutyl-α-L-aspartyl-α-methyl-L-tyrosine methyl ester, and sweetening agents comprising, as the active ingredient, anyone of the derivatives and their salts, being low-calorie sweetening agents which are excellent in stability, safety and degree of sweetness, are provided. The products to have been sweetened, comprising such above sweetening agents are also provided.

6 Claims, No Drawings

DIPEPTIDE DERIVATIVES AND SWEETENING AGENTS

BACKGROUND OF THE INVENTION

1. Field of the Invention

The present invention relates to novel dipeptide derivatives and the salts thereof, sweetening agents comprising any of them as the active ingredient, and the products to have been sweetened, which comprise any of the sweetening agents.

2. Description of the Related Art

1. Actual State of the Sweetening Agents

With advanced eating habits in these days, obesity to be caused by over-intake of sugar and its related various diseases have become problematic. Therefore, the development of low-calorie sweetening agents that replace sugar has been desired. At present, aspartame is one popular sweetening agent which is excellent in safety and quality of sweetness. However, it involves a probleme in its stability. Recently, it has been found that the alkylation of the amino group of dipeptide derivatives such as aspartame is effective in greatly increasing the degree of sweetness of the resulting derivatives, for example, as in French Patent Nos. 2,697,844 and 2,719,592, and Japanese Patent Kouhyou Publication JP-A-8-503206. However, those alkylated dipeptide derivatives are still unsatisfactory in their stability.

2. Object of the Invention

In the course of the present invention, such above problems have been also found.

The object of the present invention is to provide novel dipeptide derivatives and their salts using α-alkyl-amino acid components, which are highly stable, highly safe and can be easily obtained, and also to provide low-calorie sweetening agents containing them as the active ingredients.

SUMMARY OF THE INVENTION

The present inventors have assiduously studied a variety of N-alkyl groups and α-alkyl-amino acid components constituting dipeptide derivatives so as to solve the problems noted above, and, as a result, have found that dipeptide derivatives of the following general formula (I) can be sweetening agents which are excellent in degree of sweetness, stability and quality of sweetness for the living subjects requesting sweetness, such as humans. On the basis of this finding, they have completed the present invention.

The present invention includes a dipeptide derivative of the following formula (I), and the salt thereof:

$$R_1-NHC^1H((CH_2)_nCOOH)CONH-C^2R_2R_3-CO_2R_4 \quad (I)$$

wherein $R_1$ represents a saturated or unsaturated linear, cyclic or mixed (linear and/or cyclic) hydrocarbon group, or a saturated or unsaturated hydrocarbon group having aromatic substituent(s), both having from 1 to 13 carbon atoms, desirably a 3,3-dimethylbutyl group;

n represents 1 or 2;

$R_2$ represents a methyl group or an ethyl group, desirably a methyl group;

$R_3$ represents a phenyl group, a benzyl group, a p-hydroxybenzyl group, $CH_2SC(CH_3)_3$, $CH_2OC(CH_3)_3$, $CH_2OCH_2C(CH_3)_3$, $CH_2CH_2OC(CH_3)_3$, $CH_2CONHC(CH_3)_3$, or $CH_2NHCOC(CH_3)_3$, desirably a benzyl group or p-hydroxybenzyl group; and $R_4$ represents an alkyl group having from 1 to 4 carbon atoms, desirably a methyl group.

The configuration of the $C^1$-position carbon is desirably, (S), while that of the $C^2$-position carbon is desirably (S), (R) or (RS), more desirably (R) or (RS).

The present invention also includes as the active ingredient a sweetening agent comprising at least one substance of the above derivative and the salts thereof and a product to be sweetened such as drinks, foods, cosmetics, etc., comprising at least one of the sweetening agents.

DESCRIPTION OF THE PREFERRED EMBODIMENTS

The novel dipeptide derivatives in the present invention are the compounds represented by the above general formula (I) and defined therein. The salts thereof are also contained in the present invention.

As the salts of the compounds for the invention, for example, the salts with alkali metals such as sodium, potassium, etc., salts with alkaline earth metals such as calcium, magnesium, etc., salts with amines such as monoethanolamine, etc., salts with inorganic acids such as hydrochloric acid, sulfuric acid, etc., and salts with organic acids such as citric acid, acetic acid, etc. are cited.

The dipeptide derivatives of the present invention can be produced according to, for example, an ordinary peptide synthesis (see Izumiya, et al., Bases and Experiments of Peptide Synthesis, published by Maruzen on Jan. 20, 1985). That is, an ester of an α-alkyl-amino acid is condensed with an L-aspartic acid or glutamic acid, of which the β- or γ-carboxyl group and the amino group are protected, to give an amide, then the N-protecting groups in the resulting amide are selectively removed, thereafter the amide is subjected to reductive alkylation with an aldehyde and a reducing agent (e.g., $NaB(OAc)_3H$) (see A. F. Abdel-Magid, et al., Tetrahedron Letters, 31, 5595 (1990)), and then the remaining protecting groups in the amide are removed to obtain the intended N-alkyl-dipeptide. Alternatively, the protected amide as produced in the process noted above is deprotected to remove the protecting groups at the β- or γ-carboxyl group and the amino group, and thereafter the thus-deprotected amide is subjected to reductive alkylation with an aldehyde and a reducing agent (e.g., $H_2$/palladium-carbon) to obtain the intended N-alkyl-dipeptide. However, the methods for production of the compounds in the invention is not limited to these methods.

The sensory evaluation of the compounds and their salts in the present invention have revealed that their sweetness is strong and the quality of their sweetness is similar to that of sugar. For example, the degree of sweetness of N-3,3-dimethylbutyl-α-L-aspartyl-α-methyl-L-phenylalanine methyl ester was about 5500 times that of 4% sucrose solution; and the degree of sweetness of N-3,3-dimethylbutyl-α-L-aspartyl-α-methyl-L-tyrosine methyl ester was about 700 times that of 4% sucrose solution.

The half-life (time corresponding to 50% degradation) of N-3,3-dimethylbutyl-α-L-aspartyl-α-methyl-L-phenylalanine methyl ester in an acidic aqueous solution (in pH 3 phosphate buffer at 70° C.) was about 350 hours, and that of N-3,3-dimethylbutyl-α-L-aspartyl-α-methyl-L-tyrosine methyl. ester therein was about 347 hours. Thus, these compounds were much more stable than aspartame (its half-life is about 24 hours under the same conditions) and than N-3,3-dimethylbutyl-α-L-aspartyl-L-phenylalanine methyl ester (its half-life is about 36 to 55 hours under the same conditions) described in French Patent No. 2,697,844 and Japanese Patent Kouhyou Publication JP-A-8-503206.

When the compounds and the salts thereof in the invention are used as the sweetening agents, they may be combined with any other sweetening agents, as a matter of course, unless such combination detracts from the advantages of the invention. Such salts are safe and may be desirably edible salts for the living subjects requesting sweetness, such as humans. In the sweetening agents, they can be prepared in a combination with a suitable carrier and/or bulking agent.

In a product requesting sweetness or to be sweetened, such as drinks, foods, confectionery, pastries, chewing gums, hygiene products, toiletries, cosmetic, pharmaceuticals and veterinary products, the sweetening agents in the present invention can be used therefor, and the products using the sweetening agents are contained in the present invention. In the production of the products, the sweetening agents of the present invention are easily employed based on the arts which are ordinarily employed for the production of the products in this field.

In the present invention, there is also provided a process for giving sweetness or sweet taste to a product requesting sweetness or sweet taste, comprising the step of adding to the product, anyone of the derivatives and the salts thereof as defined in the present invention.

EXAMPLES

The following examples are given to enable those skilled in the art to more clearly understand and to practice the present invention. They should not be considered as a limitation on the scope of the present invention, but merely as being illustrative and representative thereof.

Example 1

Production of N-3,3-dimethylbutyl-α-L-aspartyl-α-methyl-L-phenylalanine methyl ester:

10 ml of methylene chloride was added to 0.310 g (1.35 mmols) of α-methyl-L-phenylalanine methyl ester hydrochloride, to which were added 0.206 ml (1.49 mmols) of triethylamine and 0.437 g (1.35 mmols) of N-t-butoxycarbonyl-L-aspartic acd β-benzyl ester while being cooled on ice to 0° C. Next, 0.285 g (1.49 mmols) of water-soluble carbodiimide hydrochloride and 0.201 g (1.49 mmols) of HOBt were added to this. The solution was heated up to room temperature, and stirred overnight. The reaction mixture was concentrated under reduced pressure, and 30 ml of ethyl acetate was added to the resulting residue. The organic layer thus separated was washed twice with 30 ml of an aqueous solution of 5% citric acid, then twice with 30 ml of an aqueous solution of 5% sodium hydrogencarbonate, and thereafter once with 30 ml of water. The thus-washed organic layer was dried with anhydrous magnesium sulfate, and filtered to remove the magnesium sulfate. The resulting filtrate was concentrated under reduced pressure to obtain 0.489 g (0.981 mmols) of N-t-butoxycarbonyl-β-O-benzylaspartyl-α-methyl-L-phenylalanine methyl ester as a colorless oily matter.

10 ml of 4 N-HCl/dioxane solution was added to 0.489 g (0.981 mmols) of N-t-butoxycarbonyl-β-O-benzylaspartyl-α-methyl-L-phenylalanine methyl ester, and the solution was stirred for 1 hour at room temperature. The reaction mixture was concentrated under reduced pressure, and 30 ml of an aqueous solution of 5% sodium hydrogencarbonate was added to the resulting residue, which was then extracted twice with 30 ml of ethyl acetate. The organic layer thus separated was washed with a saturated saline solution, then dried with anhydrous magnesium sulfate, and filtered to remove the magnesium sulfate. The resulting filtrate was concentrated under reduced pressure to obtain 0.370 g (0.929 mmols) of β-O-benzyl-α-L-aspartyl-α-methyl-L-phenylalanine methyl ester as a colorless oily matter.

0.370 g (0.929 mmols) of β-O-benzyl-α-L-aspartyl-α-methyl-L-phenylalanine methyl ester was suspended in 10 ml of tetrahydrofuran (THF), and the solution was kept at 0° C. To this were added 0.053 ml (0.929 mmols) of acetic acid, 0.117 ml (0.929 mmols) of 3,3-dimethylbutylaldehyde and 0.295 g (1.39 mmols) of NaB(OAc)$_3$H, and the solution was stirred for 1 hour at 0° C. and then overnight at room temperature. 30 ml of an aqueous solution of saturated sodium hydrogencarbonate was added to the reaction mixture, which was then extracted twice with 50 ml of ethyl acetate. The organic layer thus separated was washed with a saturated saline solution, then dried with anhydrous magnesium sulfate, and filtered to remove the magnesium sulfate. The resulting filtrate was concentrated under reduced pressure. The residue was purified with PTLC (Preparative Thin Layer Chromatography) to obtain 0.125 g (0.259 mmols) of N-3,3-dimethylbutyl-β-O-benzylaspartyl-α-methyl-L-phenylalanine methyl ester as a colorless oily matter.

0.125 g (0.259 mmols) of N-3,3-dimethylbutyl-β-O-benzylaspartyl-α-methyl-L-phenylalanine methyl ester was dissolved in 20 ml of methanol, to which was added 0.1 g of 5% Pd-carbon (having a water content of 50%). In that condition, the compound was reduced under a hydrogen atmosphere at room temperature for 3 hours. The catalyst was removed by filtration, and the filtrate was concentrated under reduced pressure. Then, the residue was dried to obtain 0.107 g (0.273 mmols) of N-3,3-dimethylbutyl-α-L-aspartyl-α-methyl-L-phenylalanine methyl ester as a white solid.

$^1$H-NMR (DMSO-d$_6$): 0.85 (s, 9H), 1.28 (s, 3H), 1.30–1.40 (m, 2H), 2.11–2.58 (m, 4H), 3.13 (dd, 2H), 3.45 (dd, 1H), 3.59 (s, 3H), 7.06–7.31 (m, 5H), 8.35 (s, 1H) ESI-MS: 393.2 (MH$^+$); Degree of Sweetness (relative to sugar): 5500 times; Stability (half-life): 350 hours (in pH 3, phosphate buffer at 70° C.)

Example 2

Production of N-3,3-dimethylbutyl-α-L-aspartyl-α-methyl-L-tyrosine methyl ester:

20 ml of methylene chloride was added to 0.698 g (2.84 mmols) of α-methyl-L-tyrosine methyl ester hydrochloride, to which were added 0.434 ml (3.12 mmols) of triethylamine and 0.918 g (2.84 mmols) of N-t-butoxycarbonyl-L-aspartic acid β-benzyl ester while being cooled on ice to 0° C. Next, 0.599 g (3.12 mmols) of water-soluble carbodiimide hydrochloride and 0.422 g (3.12 mmols) of HOBt were added to this. The solution was heated up to room temperature, and stirred overnight. The reaction mixture was concentrated under reduced pressure, and 50 ml of ethyl acetate was added to the resulting residue. The organic layer thus separated was washed twice with 50 ml of an aqueous solution of 5% citric acid, then twice with 50 ml of an aqueous solution of 5% sodium hydrogencarbonate, and thereafter once with 50 ml of water. The thus-washed organic layer was dried with anhydrous magnesium sulfate, and filtered to remove the magnesium sulfate. The resulting filtrate was concentrated under reduced pressure, and the residue was purified with PTLC to obtain 0.923 g (1.79 mmols) of N-t-butoxycarbonyl-β-O-benzylaspartyl-α-methyl-L-tyrosine methyl ester as a colorless oily matter.

10 ml of 4 N-HCl/dioxane solution was added to 0.660 g (1.28 mmols) of N-t-butoxycarbonyl-β-O-benzylaspartyl-α-methyl-L-tyrosine methyl ester, and the solution was stirred for 1 hour at room temperature. The reaction mixture was concentrated under reduced pressure, and 50 ml of an aqueous solution of 5% sodium hydrogencarbonate was added to the resulting residue, which was then extracted twice with 50 ml of ethyl acetate. The organic layer thus separated was washed with a saturated saline solution, then dried with anhydrous magnesium sulfate, and filtered to remove the magnesium sulfate. The resulting filtrate was concentrated under reduced pressure to obtain 0.317 g (0.765 mmols) of β-O-benzyl-α-L-aspartyl-α-methyl-L-tyrosine methyl ester as a colorless oily matter.

0.317 g (0.765 mmols) of β-O-benzyl-α-L-aspartyl-α-methyl-L-tyrosine methyl ester was suspended in 10 ml of THF, and the solution was kept at 0° C. To this were added 0.044 ml (0.765 mmols) of acetic acid, 0.096 ml (0.765 mmols) of 3,3-dimethylbutylaldehyde and 0.243 g (1.15 mmols) of NaB(OAc)$_3$H, and the solution was stirred for 1 hour at 0° C. and then overnight at room temperature. 30 ml of an aqueous solution of saturated sodium hydrogencarbonate was added to the reaction mixture, which was then extracted twice with 30 ml of ethyl acetate. The organic layer thus separated was washed with a saturated saline solution, then dried with anhydrous magnesium sulfate, and filtered to remove the magnesium sulfate. The resulting filtrate was concentrated under reduced pressure. The residue was purified with PTLC to obtain 0.109 g (0.219 mmols) of N-3,3-dimethylbutyl-β-O-benzyl-α-L-aspartyl-α-methyl ester as a colorless oily matter.

0.109 g (0.219 mmols) of N-3,3-dimethylbutyl-β-O-benzyl-α-L-aspartyl-α-methyl-L-tyrosine methyl ester was dissolved in 20 ml of methanol, to which was added 0.1 g of 5% Pd-carbon (having a water content of 50%). In that condition, the compound was reduced under a hydrogen atmosphere at room temperature for 1 hour. The catalyst was removed by filtration, and the filtrate was concentrated under reduced pressure. Then, the residue was dried to obtain 0.069 g (0.169 mmols) of N-3,3-dimethylbutyl-α-L-aspartyl-α-methyl-L-tyrosine methyl ester as a white solid.

$^1$H-NMR (DMSO-d$_6$): 0.86 (s, 9H), 1.26 (s, 3H), 1.30–1.37 (m, 2H), 2.21–2.57 (m, 4H), 3.00 (dd, 2H), 3.45 (dd, 1H), 3.57 (s, 3H), 6.66 (d, 2H), 6.84 (d, 2H), 8.30 (s, 1H); ESI-MS: 409.3 (MH$^+$); Degree of Sweetness (relative to sugar): 700 times; Stability (half-life): 347 hours (in pH, 3 phosphate buffer at 70° C.).

What is claimed is:

1. A dipeptide derivative of the following formula (I), or salts thereof:

$$R_1\text{—}NHC^1H((CH_2)_n COOH)CONH\text{—}C^2R_2R_3\text{—}CO_2R_4 \quad (I)$$

wherein

R$_1$ represents a saturated or unsaturated linear, cyclic or mixed hydrocarbon group, or a saturated or unsaturated hydrocarbon group having aromatic substituent(s), having from 1 to 13 carbon atoms;

n represents 1 or 2;

R$_2$ represents a methyl group or an ethyl group;

R$_3$ represents a phenyl group, a benzyl group, a p-hydroxybenzyl group, CH$_2$SC(CH$_3$)$_3$, CH$_2$OC(CH$_3$)$_3$, CH$_2$OCH$_2$C(CH$_3$)$_3$, CH$_2$CH$_2$OC(CH$_3$)$_3$, CH$_2$CONHC(CH$_3$)$_3$, or CH$_2$NHCOC(CH$_3$)$_3$; and R$_4$ represents an alkyl group having from 1 to 4 carbon atoms.

2. The derivative as claimed in claim 1, wherein the configuration of the C$^1$-position carbon is (S), while that of the C$^2$-position carbon in said general formula is (S), (R) or (RS).

3. The derivative as claimed in claim 1, wherein R$_1$ is a 3,3-dimethylbutyl group, R$_2$ is a methyl group, R$_3$ is a benzyl group, R$_4$ is a methyl group, and the configuration of the C$^2$-position carbon is (S) or (RS).

4. The derivative as claimed in claim 1, wherein R$_1$ is a 3,3-dimethylbutyl group, R$_2$ is a methyl group, R$_3$ is a p-hydroxybenzyl group, R$_4$ is a methyl group, and the configuration of the C$^2$-position carbon is (S) or (RS).

5. A sweetening agent comprising as the active ingredient, at least one substance selected from the group consisting of the derivatives of said formula (I) and salts thereof, as claimed in claim 1, in combination with an acceptable carrier, bulking agent or mixture thereof.

6. A food composition comprising the sweetening agent as claimed in claim 5, and a product to be sweetened.

* * * * *